United States Patent
Kropf et al.

(10) Patent No.: US 11,434,452 B2
(45) Date of Patent: Sep. 6, 2022

(54) DETERGENTS AND CLEANING AGENTS HAVING IMPROVED PERFORMANCE

(71) Applicant: Henkel AG & Co. KGaA, Duesseldorf (DE)

(72) Inventors: Christian Kropf, Hilden (DE); Sascha Schaefer, Mettmann (DE); Christian Umbreit, Neuss (DE); Alexander Schulz, Essen (DE); Michael Strotz, Cologne (DE); Thomas J. J. Mueller, Duesseldorf (DE); Bernhard Mayer, Neuss (DE); Melanie Denissen, Leverkusen (DE)

(73) Assignee: Henkel AG & Co. KGaA, Duesseldorf (DE)

(*) Notice: Subject to any disclaimer, the term of this patent is extended or adjusted under 35 U.S.C. 154(b) by 215 days.

(21) Appl. No.: 16/937,361

(22) Filed: Jul. 23, 2020

(65) Prior Publication Data
US 2020/0354653 A1    Nov. 12, 2020

Related U.S. Application Data

(63) Continuation of application No. PCT/EP2019/050523, filed on Jan. 10, 2019.

(30) Foreign Application Priority Data

Jan. 23, 2018 (DE) .......... 102018200960.0

(51) Int. Cl.
| | | |
|---|---|---|
| C11D 3/20 | (2006.01) | |
| C11D 3/26 | (2006.01) | |
| C11D 7/26 | (2006.01) | |
| C11D 7/32 | (2006.01) | |
| C11D 3/30 | (2006.01) | |
| C07D 403/14 | (2006.01) | |
| C07D 407/12 | (2006.01) | |
| C11D 3/28 | (2006.01) | |
| C11D 11/00 | (2006.01) | |

(52) U.S. Cl.
CPC ........... *C11D 3/30* (2013.01); *C07D 403/14* (2013.01); *C07D 407/12* (2013.01); *C11D 3/2096* (2013.01); *C11D 3/28* (2013.01); *C11D 7/267* (2013.01); *C11D 11/0017* (2013.01)

(58) Field of Classification Search
CPC ............... C11D 3/2096; C11D 7/267; C11D 11/0017; C11D 3/30
USPC ...... 510/276, 337, 312, 376, 505, 499; 8/137
See application file for complete search history.

(56) References Cited

U.S. PATENT DOCUMENTS 2,907,772 A   10/1959   Krimmel et al.

FOREIGN PATENT DOCUMENTS

| DE | 102013226003 A1 | 6/2015 |
|---|---|---|
| WO | 2007042140 A2 | 4/2007 |
| WO | 2011023716 A1 | 3/2011 |
| WO | 2015091124 A1 | 6/2015 |

OTHER PUBLICATIONS

Fox, Raymond C. et al., "Bis(5-Hydroxy-2-Hydroxymethyl-Pyran-4-One-6-yl)Methane: A Novel Ligand for the Intracellular Mobilisation of Ferritin-Bound Iron". Bioorganic & Medicinal Chemistry Letters, vol. 8, pp. Jan. 1998, 443-446, Elsevier Science Ltd.
Benelli, Cristiano et al. "Di-maltol-polyamine Ligands to Form Heterotrinuclear Metal Complexes: Solid State, Aqueous Solution and Magnetic Characterization". Dalton Transactions, vol. 42, No. 16, Jan. 1, 2013, pp. 5848-5859. The Royal Society of Chemistry. DOI: 10.1039/c3dt32130d. ISSN: 1477-9226, XP055361559.
International Search Report PCT/EP2019/050523 Completion Date: Apr. 2, 2019 dated Apr. 25, 2019 3 pages.

*Primary Examiner* — Gregory R Delcotto
(74) *Attorney, Agent, or Firm* — Bojuan Deng

(57) ABSTRACT

The present invention relates to the use of substituted bis-4H-pyranonyl compounds in which the 4H-pyranonyl units are combined with heteroalkyl groups, in detergents and cleaning agents, for improving detergent or cleaning performance with respect to bleachable stains.

19 Claims, No Drawings

DETERGENTS AND CLEANING AGENTS HAVING IMPROVED PERFORMANCE

FIELD OF THE INVENTION

The present invention relates to the use of particular bis-4H-pyranonylmethanes in washing and cleaning agents for improving the washing or cleaning performance.

BACKGROUND OF THE INVENTION

Whereas the formulation of powdered washing and cleaning agents that contain bleaching agent does not pose any problems nowadays, the formulation of stable, liquid washing and cleaning agents that contain bleaching agent continues to pose a problem. Correspondingly, due to the conventional lack of bleaching agent in liquid washing and cleaning agents, stains which are normally removed in particular due to the contained bleaching agent are often only insufficiently removed. A similar problem also exists for bleaching agent-free color detergents in which the bleaching agent is omitted in order to protect the dyes in the textile and prevent the bleaching thereof. The lack of bleaching agent is made more problematic by the fact that, instead of removing bleachable stains which are normally at least partially removed by the peroxygen-based bleaching agent, instead often the removability of the stain is even intensified and/or worsened as a result of the washing process, and this should not least be attributed to initiated chemical reactions which can consist, for example, in the polymerization of particular dyes contained in the stains.

Problems of this kind occur in particular on stains which contain polymerizable substances. The polymerizable substances are primarily polyphenolic dyes, preferably flavonoids, in particular from the class of anthocyanidins or anthocyanins. The stains may have been caused in particular by food products or drinks which contain corresponding dyes. The stains can be in particular marks from fruit or vegetables or even red wine marks, which contain in particular polyphenolic dyes, particularly those from the class of anthocyanidins or anthocyanins.

The international patent application WO 2011/023716 A1 discloses, for example, the use of gallic acid esters such as propyl gallate in washing and cleaning agents for improved removal of stains which contain polymerizable substances.

The use of 4-pyridinones that are substituted at the N atom optionally with organic groups, such as the methyl, ethyl, propyl, phenyl, naphthyl or carboxyethyl group, for the removal of stains from textiles is known from international patent application WO 2007/042140 A2.

The dimer of kojic acid and its complex formation property for iron was described by R. C. Fox and P. D. Taylor in Bioorganic & Medicinal Chem. Lett. 8 (1998), 443-446. Improving the washing or cleaning performance of washing and cleaning agents with respect to bleachable stains by means of bis-pyranonylmethanes is known from international patent application WO 2015/091124 A1.

BRIEF SUMMARY OF THE INVENTION

Surprisingly, it has now been found that, by using particular bis-4H-pyranonyl compounds in which the 4H-pyranonyl units are connected by heteroalkyl groups, the washing or cleaning performance of washing or cleaning agents can be greatly improved, in particular with regard to bleachable stains.

The present invention therefore first relates to the use of compounds of general formula (I),

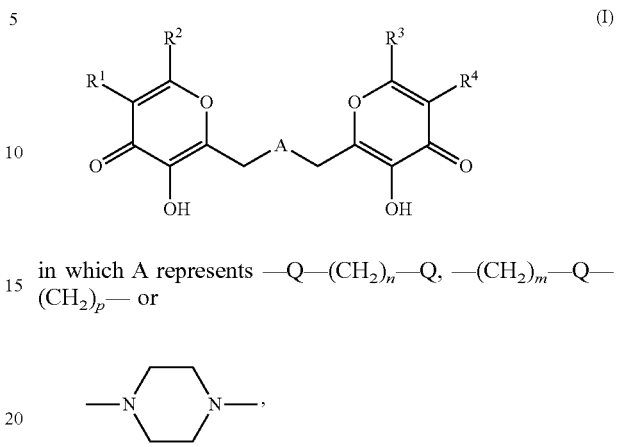

in which A represents —Q—$(CH_2)_n$—Q, —$(CH_2)_m$—Q—$(CH_2)_p$— or

—N⏜N—,

Q represents O, $N(R^5)$ or $N^+H(R^5)X^-$, $R^1$, $R^2$, $R^3$, $R^4$ and $R^5$ represent, independently of one another, hydrogen or a straight-chain or branched alkyl group having 1 to 4 C atoms, $X^-$ represents a charge-balancing anion, n represents a number from 1 to 10, and m and p represent, independently of one another, numbers from 0 to 7, in washing or cleaning agents in order to improve the washing or cleaning performance on bleachable stains.

The bleachable stains typically contain polymerizable substances, in particular polymerizable dyes, the polymerizable dyes preferably being polyphenolic dyes, in particular flavonoids, more particularly anthocyanidins or anthocyanins or oligomers of said compounds. In addition to removing stains in the colors green, yellow, red or blue, it is also possible to remove stains in intermediate colors, in particular violet, lilac, brown, purple or pink, and also to remove stains which have a green, yellow, red, violet, lilac, brown, purple, pink or blue hue but do not substantially consist entirely of this color. The mentioned colors can in particular also each be light or dark. The bleachable stains are preferably stains, in particular marks from grass, fruit or vegetables, in particular also stains caused by food products, such as spices, sauces, chutneys, curries, purees and jams, or drinks, such as coffee, tea, wine and juices, which contain the corresponding green, yellow, red, violet, lilac, brown, purple, pink and/or blue dyes.

The stains to be removed according to the invention can in particular be caused by cherries, morellos, grapes, apples, pomegranates, chokeberries, plums, sea buckthorns, acai, kiwifruit, mango, grass, or berries, in particular caused by redcurrants, blackcurrants, elderberries, blackberries, raspberries, blueberries, lingonberries, cranberries, strawberries or bilberries, or by coffee, tea, red cabbage, blood orange, eggplant, tomato, carrot, beetroot, spinach, bell pepper, red or blue potato or red onion.

Compounds of the general formula (I) can be prepared from maltol by halogenation of the methyl group and reaction with bisamines or by oxidation of the methyl group to form the aldehyde, subsequent reduction to form the alcohol, optionally activation of the alcohol, for example as a methanesulfonic acid derivative, and subsequent reaction with dihalides. Compounds where m>0 and/or p>0 are obtained, for example, by combining these methods starting from maltol or homologs of maltol which carry C atoms in the 2-position alkyl groups where m+1 or p+1.

In the compounds of general formula (I), $R^1$ and $R^3$ and/or $R^2$ and $R^4$ are preferably the same. The preferred compounds of general formula (I) also include those in which $R^1$, $R^2$, $R^3$ and $R^4$ are hydrogen, and/or $R^5$ is a methyl group. n is preferably a number from 1 to 6, in particular 1 to 3. The anion $X^-$, if present, is preferably selected from lactate, citrate, tartrate or succinate, perchlorate, tetrafluoroborate, hexafluorophosphate, alkyl sulfonate, alkyl sulfate, hydrogen sulfate, sulfate, dihydrogen phosphate, hydrogen phosphate, phosphate, isocyanate, thiocyanate, nitrate, fluoride, chloride, bromide, hydrogen carbonate or carbonate, the charge balance being ensured in polyvalent anions by correspondingly more cationic substances according to the invention or optionally by the presence of additional cations such as sodium, potassium or ammonium ions.

The use according to the invention of the compound of general formula (I) preferably occurs in washing or cleaning agents by the compound being used in an amount of from 0.001 wt. % to 20 wt. %, in particular in an amount of from 0.01 wt. % to 10 wt. %, with the quantities in "wt. %" in each case here and in the following being based on the weight of the total washing or cleaning agent. The invention therefore further relates to a washing or cleaning agent containing a compound of the general formula (I) described above in an amount of preferably from 0.001 wt. % to 20 wt. %, in particular from 0.01 wt. % to 10 wt. %, the preferred embodiments of the use according to the invention described above or below also applying to this subject matter of the invention. An agent of this kind is used in conventional automatic or manual washing or cleaning methods in which stained laundry or a stained hard surface is exposed to an aqueous liquor containing the agent for the purpose of removing the stain from the textile or hard surface.

The washing or cleaning agent can be present in any dosage form established in the prior art and/or in any expedient dosage form. These include, for example, solid, powdered, liquid, gel or pasty dosage forms, optionally also consisting of a plurality of phases; these also include, for example: extrudates, granules, tablets or pouches, both packaged in bulk containers and in portions.

DETAILED DESCRIPTION OF THE INVENTION

In a preferred embodiment, the use according to the invention preferably occurs in a washing and cleaning agent that does not contain oxidative bleaching agents. This is understood to mean that the agent does not contain oxidative bleaching agents in the narrower sense, which include hypochlorites, hydrogen peroxide or substances that yield hydrogen peroxide, and peroxoacids; the agent preferably does not comprise bleach activators and/or bleach catalysts either.

In a particularly preferred embodiment, the washing agent is a liquid laundry detergent.

In a further particularly preferred embodiment, the washing agent is a powdered or liquid color detergent, i.e. a laundry detergent for colored textiles.

In addition to the active ingredient which is essential to the invention, the washing or cleaning agents can also contain other conventional components of washing or cleaning agents, in particular laundry detergents, in particular selected from the group of builders and surfactants, and preferably polymers, enzymes, disintegration auxiliaries, fragrances and perfume carriers.

The builders include in particular zeolites, silicates, carbonates, organic cobuilders and also phosphates, provided there are no ecological prejudices against the use thereof.

The microcrystalline, synthetic and bound water-containing zeolite is preferably zeolite A and/or zeolite P. Zeolite MAP® (commercial product from the company Crosfield) is also possible as zeolite P. However, zeolite X and mixtures of zeolite A, X and/or P are also suitable. A co-crystallizate of zeolite X and zeolite A (approx. 80 wt. % zeolite X) which can be described by the formula

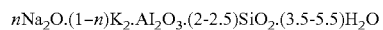

$n\text{Na}_2\text{O}.(1-n)\text{K}_2.\text{Al}_2\text{O}_3.(2-2.5)\text{SiO}_2.(3.5-5.5)\text{H}_2\text{O}$ is commercially available and can be used in the context of the present invention, for example. The zeolite can in this case be used as a builder in a granular compound and used for a type of "powdering" of a granular mixture, preferably of a mixture to be compressed, the two ways typically being used to incorporate the zeolite into the premixture. Zeolites can have an average particle size of less than 10 μm (volume distribution; measuring method: Coulter counter) and preferably contain from 18 wt. % to 22 wt. %, in particular from 20 wt. % to 22 wt. %, of bound water.

Crystalline layered silicates of general formula $\text{NaMSi}_x\text{O}_{2x+}.y\text{H}_2\text{O}$ can also be used, where M represents sodium or hydrogen, x is a number from 1.9 to 22, preferably from 1.9 to 4, with 2, 3, or 4 being particularly preferred values for x, and y represents a number from 0 to 33, preferably from 0 to 20. The crystalline layered silicates of formula $\text{NaMSi}_x\text{O}_{2x+1}.y\text{H}_2\text{O}$ are distributed for example by the company Clariant GmbH (Germany) under the trade name Na-SKS. Examples of these silicates are Na-SKS-1 ($\text{Na}_2\text{Si}_{22}\text{O}_{45}.x\text{H}_2\text{O}$, kenyaite), Na-SKS-2 ($\text{Na}_2\text{Si}_{14}\text{O}_{29}.x\text{H}_2\text{O}$, magadiite), Na-SKS-3 ($\text{Na}_2\text{Si}_8\text{O}_{17}.x\text{H}_2\text{O}$) or Na-SKS-4 ($\text{Na}_2\text{Si}_4\text{O}_9.x\text{H}_2\text{O}$, makatite).

Crystalline phyllosilicates of formula $\text{NaMSi}_x\text{O}_{2x+1}.y\text{H}_2\text{O}$, in which x represents 2, are preferred. In particular, both β- and δ-sodium disilicates $\text{Na}_2\text{Si}_2\text{O}_5.y\text{H}_2\text{O}$ and also especially Na-SKS-5 (α-$\text{Na}_2\text{Si}_2\text{O}_5$), Na-SKS-7 (β-$\text{Na}_2\text{Si}_2\text{O}_5$, natrosilite), Na-SKS-9 ($\text{NaHSi}_2\text{O}_5.\text{H}_2\text{O}$), Na-SKS-10 ($\text{NaHSi}_2\text{O}_5.3\text{H}_2\text{O}$, kanemite), Na-SKS-11 (t-$\text{Na}_2\text{Si}_2\text{O}_5$) and Na-SKS-13 ($\text{NaHSi}_2\text{O}_5$), in particular however Na-SKS-6 (δ-$\text{Na}_2\text{Si}_2\text{O}_5$), are preferred. Washing or cleaning agents preferably contain a proportion by weight of the crystalline layered silicate of formula $\text{NaMSi}_x\text{O}_{2x+1}.y\text{H}_2\text{O}$ of from 0.1 wt. % to 20 wt. %, preferably from 0.2 wt. % to 15 wt. %, and in particular from 0.4 wt. % to 10 wt. %.

Amorphous sodium silicates with an $\text{Na}_2\text{O}:\text{SiO}_2$ modulus of from 1:2 to 1:3.3, preferably from 1:2 to 1:2.8, and in particular from 1:2 to 1:2.6, can also be used which preferably exhibit retarded dissolution and secondary washing properties. The retarded dissolution compared to conventional amorphous sodium silicates can in this case have been caused in a variety of ways, for example by way of surface treatment, compounding, compacting/compression or overdrying. "Amorphous" is understood to mean that, in X-ray diffraction experiments, the silicates do not supply any sharp X-ray reflexes, such as those that are typical of crystalline substances, but at best cause one or more maxima of the scattered X-rays, which have a width of several degree units of the diffraction angle.

Alternatively or in combination with the aforementioned amorphous sodium silicates, X-ray amorphous silicates can be used, the silicate particles of which supply washed-out or even sharp diffraction maxima in electron diffraction experiments. This is to be interpreted such that the products comprise microcrystalline regions measuring 10 to several hundred nm, with values up to a maximum of 50 nm, and in particular up to a maximum of 20 nm, being preferred. X-ray amorphous silicates of this kind likewise exhibit retarded dissolution compared to conventional water glasses. Compressed/compacted amorphous silicates, compounded amorphous silicates and overdried X-ray amorphous silicates are particularly preferred.

Said silicate(s), preferably alkali silicates, particularly preferably crystalline or amorphous alkali disilicates, are, if present, contained in washing or cleaning agents in amounts of from 3 wt. % to 60 wt. %, preferably from 8 wt. % to 50 wt. %, and in particular from 20 wt. % to 40 wt. %.

It is also possible to use the generally known phosphates as builders, provided that the use thereof should not be avoided for ecological reasons. Among the large number of commercially available phosphates, the alkali metal phosphates, particularly preferably pentasodium triphosphate and pentapotassium triphosphate (sodium tripolyphosphate and potassium tripolyphosphate), are the most important in the washing and cleaning agent industry.

Alkali metal phosphate is in this case the universal term for the alkali metal (in particular sodium and potassium) salts of the various phosphoric acids, of which metaphosphoric acid $(HPO_3)n$ and orthophosphoric acid $H_3PO_4$ can be distinguished in addition to higher-molecular-weight representatives. The phosphates in this case combine several advantages: they act as alkali carriers, prevent lime deposits on machine parts or lime encrustations in fabrics and in so doing contribute to cleaning performance. Particularly industrially important phosphates are pentasodium triphosphate, $Na_5P_3O_{10}$ (sodium tripolyphosphate), and the corresponding potassium salt pentapotassium triphosphate, $K_5P_3O_{10}$ (potassium tripolyphosphate). Sodium potassium tripolyphosphates are also preferably used. If phosphates are used in washing or cleaning agents, preferred agents therefore contain said phosphate(s), preferably alkali metal phosphate(s), particularly preferably pentasodium triphosphate or pentapotassium triphosphate (sodium tripolyphosphate or potassium tripolyphosphate), in amounts of from 5 wt. % to 80 wt. %, preferably from 15 wt. % to 75 wt. %, and in particular from 20 wt. % to 70 wt. %.

Alkali carriers can also be used. Alkali carriers can include, for example, alkali metal hydroxides, alkali metal carbonates, alkali metal hydrogen carbonates, alkali metal sesquicarbonates, the mentioned alkali silicates, alkali metasilicates, and mixtures of the aforementioned substances, it being preferable to use alkali carbonates, in particular sodium carbonate, sodium hydrogen carbonate or sodium sesquicarbonate. A builder system containing a mixture of tripolyphosphate and sodium carbonate can be particularly preferred. Due to its low chemical compatibility with the other ingredients of washing or cleaning agents, in comparison with other builder substances, the alkali metal hydroxides are conventionally only used in small amounts, preferably in amounts below 10 wt. %, more preferably below 6 wt. %, particularly preferably below 4 wt. %, and in particular below 2 wt. %. Agents which contain, based on the total weight thereof, less than 0.5 wt. % and in particular no alkali metal hydroxides are particularly preferred. It is also preferred to use carbonate(s) and/or hydrogen carbonate(s), preferably alkali carbonate(s), particularly preferably sodium carbonate, in amounts of from 2 wt. % to 50 wt. %, preferably from 5 wt. % to 40 wt. %, and in particular from 7.5 wt. % to 30 wt. %.

Polycarboxylates/polycarboxylic acids, polymeric polycarboxylates, aspartic acid, polyacetals, dextrins and phosphonates are particularly noteworthy as organic builders. The polycarboxylic acids that can be used in the form of the free acids and/or the sodium salts thereof can be used, for example, with polycarboxylic acids being understood to mean carboxylic acids that carry more than one acid function. These include, for example, citric acid, adipic acid, succinic acid, glutaric acid, malic acid, tartaric acid, maleic acid, fumaric acid, saccharic acids, aminocarboxylic acids, nitrilotriacetic acid (NTA), provided that the use thereof is not objectionable for ecological reasons, and mixtures thereof. In addition to their builder effect, the free acids typically also have the property of being an acidification component and are thus also used for setting a lower and milder pH of washing or cleaning agents. Citric acid, succinic acid, glutaric acid, adipic acid, gluconic acid, and any mixtures thereof are particularly noteworthy here. Polymeric polycarboxylates are also suitable as builders. These are, for example, the alkali metal salts of polyacrylic acid or polymethacrylic acid, for example those having a relative molecular mass of from 500 g/mol to 70,000 g/mol. Polyacrylates which preferably have a molecular mass of from 2,000 g/mol to 20,000 g/mol are particularly suitable. Due to their superior solubility, the short-chain polyacrylates which have molar masses of from 2,000 g/mol to 10,000 g/mol, and particularly preferably from 3,000 g/mol to 5,000 g/mol, can be preferred from this group. In addition, copolymeric polycarboxylates are suitable, in particular those of acrylic acid with methacrylic acid and of acrylic acid or methacrylic acid with maleic acid. Copolymers of acrylic acid with maleic acid which contain from 50 wt. % to 90 wt. % acrylic acid and from 50 wt. % to 10 wt. % maleic acid have also been found to be particularly suitable. The relative molecular mass thereof, based on free acids, is generally from 2,000 g/mol to 70,000 g/mol, preferably from 20,000 g/mol to 50,000 g/mol, and in particular from 30,000 g/mol to 40,000 g/mol. To improve the water solubility, the polymers can also contain allyl sulfonic acids, such as allyloxybenzene sulfonic acid and methallyl sulfonic acid, as a monomer. The (co)polymeric polycarboxylates can be used as a solid or in aqueous solution. The content of (co)polymeric polycarboxylates in washing or cleaning agents is preferably from 0.5 wt. % to 20 wt. %, and in particular from 3 wt. % to 10 wt. %.

Biodegradable polymers composed of more than two different monomer units are also particularly preferred, such as polymers which contain salts of acrylic acid and of maleic acid and vinyl alcohol or vinyl alcohol derivatives as monomers, or polymers which contain salts of acrylic acid and of 2-alkylallyl sulfonic acid and sugar derivatives as monomers. Further preferred copolymers are those which have acrolein and acrylic acid/acrylic acid salts or acrolein and vinyl acetate as monomers. Polymeric aminodicarboxylic acids, the salts thereof or the precursors thereof should likewise be mentioned as further preferred builders. Polyaspartic acids and/or the salts thereof are particularly preferred.

A further class of substances having builder properties is that of phosphonates. These are the salts of in particular hydroxyalkane phosphonic acids or aminoalkane phosphonic acids. Of the hydroxyalkane phosphoric acids, 1-hydroxyethane-1,1-diphosphonic acid (HEDP) is particularly important. It is used in particular as a sodium salt, the disodium salt reacting neutral and the tetrasodium salt reacting alkaline. Possible aminoalkane phosphonic acids include in particular ethylenediamine tetramethylene phosphonic acid (EDTMP), diethylenetriamine pentamethylene phosphonic acid (DTPMP) and the higher homologs thereof.

They are used in particular in the form of the neutrally reacting sodium salts, for example as a hexasodium salt of EDTMP or as a heptasodium salt and octasodium salt of DTPMP. Mixtures of the mentioned phosphonates can also be used as organic builders. In particular, the aminoalkane phosphonates additionally have a pronounced heavy-metal-binding power.

Further suitable builders are polyacetals which can be obtained by reacting dialdehydes with polyol carboxylic acids having 5 to 7 C atoms and at least 3 hydroxyl groups. Preferred polyacetals are obtained from dialdehydes such as glyoxal, glutaraldehyde, terephthalaldehyde and mixtures thereof, and from polyol carboxylic acids such as gluconic acid and/or glucoheptonic acid.

Further suitable organic builders are dextrins, for example oligomers or polymers of carbohydrates, which can be obtained by the partial hydrolysis of starches.

The hydrolysis can be carried out according to customary methods, for example acid- or enzyme-catalyzed methods. These dextrins are preferably hydrolysis products having an average molar mass in the range of from 400 g/mol to 500,000 g/mol. In this case, a polysaccharide having a dextrose equivalent (DE) in the range of from 0.5 to 40, in particular from 2 to 30, is preferred, DE being a customary measure for the reducing effect of a polysaccharide compared to dextrose, which has a DE of 100. It is possible to use both maltodextrins having a DE between 3 and 20 and dried glycose syrups having a DE between 20 and 37, and what are known as yellow dextrins and white dextrins having higher molar masses in the range of from 2000 g/mol to 30,000 g/mol. Oxidized derivatives of dextrins of this type are the reaction products thereof with oxidizing agents which are capable of oxidizing at least one alcohol function of the saccharide ring to form a carboxylic acid function.

Oxydisuccinates and other derivatives of disuccinates, preferably ethylenediamine disuccinate, are further suitable cobuilders. In this case, ethylenediamine-N,N'-disuccinate (EDDS) is preferably used in the form of the sodium or magnesium salts thereof. Glycerol disuccinates and glycerol trisuccinates are also preferred in this context. If desired, suitable amounts for use in particular in zeolite-containing and/or silicate-containing formulations are from 3 wt. % to 15 wt. %.

Further organic cobuilders that can be used are, for example, acetylated hydroxycarboxylic acids or the salts thereof, which optionally can also be present in lactone form and comprise at least 4 carbon atoms and at least one hydroxy group, as well as no more than two acid groups.

Furthermore, all compounds that are able to form complexes with alkaline earth ions can be used as builders.

Washing and cleaning agents can contain non-ionic, anionic, cationic and/or amphoteric surfactants.

All non-ionic surfactants that are known to a person skilled in the art can be used as non-ionic surfactants. Washing or cleaning agents particularly preferably contain non-ionic surfactants from the group of alkoxylated alcohols. Non-ionic surfactants that are preferably used are alkoxylated, advantageously ethoxylated, in particular primary alcohols having preferably 8 to 18 C atoms and, on average, 1 to 12 mol of ethylene oxide (EO) per mol of alcohol, in which the alcohol functional group can be linear or preferably methyl-branched in the 2 position, or can contain linear and methyl-branched functional groups in admixture, as are usually present in oxo alcohol functional groups. However, alcohol ethoxylates having linear functional groups of alcohols of native origin having 12 to 18 C atoms, for example of coconut alcohol, palm alcohol, tallow fatty alcohol or oleyl alcohol, and an average of 2 to 8 EO per mol of alcohol, are particularly preferred. Preferred ethoxylated alcohols include $C_{12-14}$ alcohols having 3 EO or 4 EO, $C_{9-11}$ alcohols having 7 EO, $C_{13-15}$ alcohols having 3 EO, 5 EO, 7 EO or 8 EO, $C_{12-18}$ alcohols having 3 EO, 5 EO or 7 EO, and mixtures thereof, such as mixtures of $C_{12-14}$ alcohol having 3 EO and $C_{12-18}$ alcohol having 5 EO. The degrees of ethoxylation specified represent statistical averages that can correspond to an integer or a fractional number for a specific product. Preferred alcohol ethoxylates have a narrowed homolog distribution (narrow range ethoxylates, NRE).

Alternatively or in addition to these non-ionic surfactants, fatty alcohols having more than 12 EO can also be used. Examples of these are tallow fatty alcohols having 14 EO, 25 EO, 30 EO or 40 EO. Moreover, alkyl glycosides of general formula $RO(G)_x$ can also be used as further non-ionic surfactants, in which formula R corresponds to a primary straight-chain or methyl-branched aliphatic functional group, in particular an aliphatic functional group that is methyl-branched in the 2 position, having 8 to 22, preferably 12 to 18, C atoms, and G is the symbol that represents a glycose unit having 5 or 6 C atoms, preferably glucose. The degree of oligomerization x, which indicates the distribution of monoglycosides and oligoglycosides, is any number between 1 and 10; x is preferably between 1.2 and 1.4.

Another class of preferably used non-ionic surfactants, which are used either as the sole non-ionic surfactant or in combination with other non-ionic surfactants, are alkoxylated, preferably ethoxylated or ethoxylated and propoxylated fatty acid alkyl esters, preferably having 1 to 4 carbon atoms in the alkyl chain.

Non-ionic surfactants of the amine oxide type, for example N-cocoalkyl-N,N-dimethylamine oxide and N-tallow alkyl-N,N-dihydroxyethylamine oxide, and of the fatty acid alkanolamide type can also be used. The quantity of these non-ionic surfactants is preferably no more than that of the ethoxylated fatty alcohols, in particular no more than half thereof.

Further suitable surfactants are polyhydroxy fatty acid amides of the formula

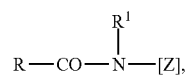

in which R represents an aliphatic acyl functional group having 6 to 22 carbon atoms, $R^1$ represents hydrogen, an alkyl functional group or hydroxyalkyl functional group having 1 to 4 carbon atoms, and [Z] represents a linear or branched polyhydroxyalkyl functional group having 3 to 10 carbon atoms and 3 to 10 hydroxyl groups. The polyhydroxy fatty acid amides are known substances that can usually be obtained by the reductive amination of a reducing sugar with ammonia, an alkylamine or an alkanolamine, and subsequent acylation with a fatty acid, a fatty acid alkyl ester or a fatty acid chloride. The group of polyhydroxy fatty acid amides also includes compounds of formula

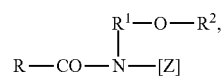

in which R represents a linear or branched alkyl or alkenyl functional group having 7 to 12 carbon atoms, $R^1$ represents a linear, branched or cyclic alkyl functional group or an aryl functional group having 2 to 8 carbon atoms, and $R^2$ represents a linear, branched or cyclic alkyl functional group or an aryl functional group or an oxy alkyl functional group having 1 to 8 carbon atoms, $C_{1-4}$ alkyl or phenyl functional groups being preferred, and [Z] represents a linear polyhydroxy alkyl functional group, the alkyl chain of which is substituted with at least two hydroxyl groups, or alkoxylated, preferably ethoxylated or propoxylated derivatives of this functional group. [Z] is preferably obtained by the reductive amination of a reduced sugar, for example glucose, fructose, maltose, lactose, galactose, mannose or xylose. The N-alkoxy-substituted or N-aryloxy-substituted compounds can be converted, in the presence of an alkoxide as the catalyst, into the desired polyhydroxy fatty acid amides by reacting these with fatty acid methyl esters.

In cleaning agents, non-ionic surfactants from the group of alkoxylated alcohols, particularly preferably from the group of mixed alkoxylated alcohols and in particular from the group of EO/AO/EO non-ionic surfactants, or PO/AO/PO non-ionic surfactants, especially PO/EO/PO non-ionic surfactants, are particularly preferred. Such PO/EO/PO non-ionic surfactants are also characterized by good foam control.

Anionic surfactants that are used are those of the sulfonate and sulfate types, for example. Surfactants of the sulfonate type that can be used are preferably $C_{9-13}$ alkylbenzene sulfonates, olefin sulfonates, i.e. mixtures of alkene and hydroxyalkane sulfonates, and disulfonates, as obtained, for example, from $C_{12-18}$ monoolefins having a terminal or internal double bond by way of sulfonation with gaseous sulfur trioxide and subsequent alkaline or acid hydrolysis of the sulfonation products. Also suitable are alkane sulfonates obtained from $C_{12-18}$ alkanes, for example, by way of sulfochlorination or sulfoxidation with subsequent hydrolysis or neutralization. Likewise, the esters of α-sulfofatty acids (ester sulfonates) are suitable, for example the α-sulfonated methyl esters of hydrogenated coconut fatty acids, palm kernel fatty acids or tallow fatty acids.

Sulfated fatty acid glycerol esters are further suitable anionic surfactants. Fatty acid glycerol esters are understood to mean the monoesters, diesters and triesters and the mixtures thereof, as they are obtained during production by way of esterification of a monoglycerol having 1 to 3 mol of fatty acid or during the transesterification of triglycerides having 0.3 to 2 mol of glycerol. Preferred sulfated fatty acid glycerol esters are in this case the sulfation products of saturated fatty acids having 6 to 22 carbon atoms, for example of caproic acid, caprylic acid, capric acid, myristic acid, lauric acid, palmitic acid, stearic acid or behenic acid.

The alkali salts and in particular the sodium salts of the sulfuric acid half-esters of $C_{12}$-$C_{18}$ fatty alcohols, for example from coconut fatty alcohol, tallow fatty alcohol, lauryl alcohol, myristyl alcohol, cetyl alcohol or stearyl alcohol, or of $C_{10}$-$C_{20}$ oxo alcohols and the half-esters of secondary alcohols having these chain lengths are preferred as alk(en)yl sulfates. Alk(en)yl sulfates of the mentioned chain length that contain a synthetic straight-chain alkyl functional group prepared on a petrochemical basis and have a degradation behavior similar to that of the adequate compounds based on fatty chemical raw materials are also preferred. From a washing perspective, Cu—Cm alkyl sulfates, $C_{12}$-$C_{15}$ alkyl sulfates and $C_{14}$-$C_{15}$ alkyl sulfates are preferred.

The sulfuric acid monoesters of straight-chain or branched $C_{7-21}$ alcohols ethoxylated with 1 to 6 mol of ethylene oxide, such as 2-methyl-branched $C_{9-11}$ alcohols having, on average, 3.5 mol ethylene oxide (EO) or $C_{12-18}$ fatty alcohols having 1 to 4 EO, are also suitable. Due to the high foaming behavior thereof, they are used in cleaning agents only in relatively small amounts, for example in amounts of from 1 wt. % to 5 wt. %.

Further suitable anionic surfactants are also the salts of alkyl sulfosuccinic acid, which are also referred to as sulfosuccinates or as sulfosuccinic acid esters and represent the monoesters and/or diesters of sulfosuccinic acid with alcohols, preferably fatty alcohols, and in particular ethoxylated fatty alcohols. Preferred sulfosuccinates contain $C_{8-18}$ fatty alcohol functional groups or mixtures of these. In particular, preferred sulfosuccinates contain a fatty alcohol functional group that is derived from ethoxylated fatty alcohols which, considered per se, represent non-ionic surfactants. Particularly preferred, in turn, are sulfosuccinates, the fatty alcohol functional groups of which derive from ethoxylated fatty alcohols exhibiting a restricted homolog distribution. Likewise, it is also possible to use alk(en)yl succinic acid having preferably 8 to 18 carbon atoms in the alk(en)yl chain, or the salts thereof.

Further anionic surfactants that can also be used are in particular soaps. Saturated fatty acid soaps are suitable, such as the salts of lauric acid, myristic acid, palmitic acid, stearic acid, hydrogenated erucic acid and behenic acid, and in particular soap mixtures derived from natural fatty acids, such as coconut fatty acids, palm kernel fatty acids or tallow fatty acids.

The anionic surfactants, including the soaps, can be present in the form of the sodium, potassium or ammonium salts thereof, or as soluble salts of organic bases, such as monoethanolamine, diethanolamine or triethanolamine. The anionic surfactants are preferably present in the form of the sodium or potassium salts thereof, in particular in the form of the sodium salts.

Instead of the mentioned surfactants or in conjunction therewith, cationic and/or amphoteric surfactants can also be used.

Cationic compounds of the following formulas can be used as cationic active substances, for example:

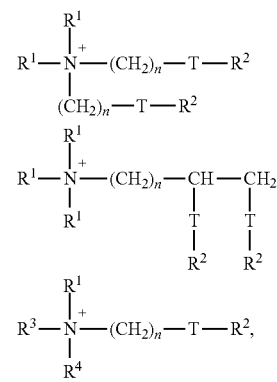

where each group $R^1$ is selected, independently of one another, from $C_{1-6}$ alkyl groups, $C_{1-6}$ alkenyl groups or $C_{1-6}$ hydroxyalkyl groups; each group $R^2$ is selected, independently of one another, from $C_{8-28}$ alkyl groups or $C_{8-28}$ alkenyl groups; $R^3=R^1$ or $(CH_2)_n$-T-$R^2$; $R^4=R^1$ or $R^2$ or $(CH_2)_n$-$R^2$; T=—$CH_2$—, —O—CO— or —CO—O—; and n is an integer from 0 to 5.

Textile-softening compounds can be used in order to care for the textiles and improve the textile properties such as a softer "feel" (softening) and lower electrostatic charge (increased wearing comfort). The active ingredients of these formulations are quaternary ammonium compounds having two hydrophobic functional groups, such as distearyl dimethyl ammonium chloride, which is however, due to the insufficient biodegradability thereof, increasingly being replaced by quaternary ammonium compounds which contain ester groups in the hydrophobic functional groups thereof as predetermined breaking points for biodegradation.

"Esterquats" of this kind that have improved biodegradability can be obtained, for example, by esterifying mixtures of methyldiethanolamine and/or triethanolamine with fatty acids and subsequently quaternizing the reaction products with alkalizing agents in a manner known per se. Dimethylol ethylene urea is also suitable as a finish.

Enzymes can be used to increase the performance of washing or cleaning agents. These include, in particular, proteases, amylases, lipases, hemicellulases, cellulases, perhydrolases, or oxidoreductases, as well as preferably mixtures thereof. These enzymes are in principle of natural origin; starting from the natural molecules, improved variants for use in washing and cleaning agents are available, which are preferably used accordingly. Washing or cleaning agents contain enzymes preferably in total amounts of from $1 \times 10^{-6}$ wt. % to 5 wt. %, based on active protein. The protein concentration can be determined with the aid of known methods, for example the BCA method or the Biuret method.

Among the proteases, the subtilisin-type proteases are preferred. Examples of these are the subtilisins BPN' and Carlsberg, as well as the further-developed forms thereof, protease PB92, subtilisins 147 and 309, the alkaline protease from *Bacillus lentus*, subtilisin DY, and the enzymes thermitase, proteinase K and proteases TW3 and TW7, which belong to the subtilases but no longer to the subtilisins in the narrower sense.

Examples of amylases that can be used are α-amylases from *Bacillus licheniformis*, from *B. amyloliquefaciens*, from *B. stearothermophilus*, from *Aspergillus niger* and *A. oryzae*, as well as the further developments of the above-mentioned amylases that have been improved for use in washing and cleaning agents. Others that are particularly noteworthy for this purpose are the α-amylases from *Bacillus* sp. A 7-7 (DSM 12368) and cyclodextrin glucanotransferase (CGTase) from *B. agaradherens* (DSM 9948).

Lipases or cutinases can be used due to the tyiglyceride-cleaving activity thereof. These include, for example, the lipases that can originally be obtained from *Humicola lanuginosa* (*Thermomyces lanuginosus*) or have been further developed therefrom, in particular those having the amino acid exchange D96L. Moreover, the cutinases which have been originally isolated from *Fusarium solani pisi* and *Humicola insolens* can also be used, for example. Lipases and/or cutinases of which the starting enzymes have been isolated originally from *Pseudomonas mendocina* and *Fusarium solanii* can also be used.

Moreover, enzymes can be used which can be grouped together under the term "hemicellulases". These include, for example, mannanases, xanthan lyases, pectin lyases (=pectinases), pectinesterases, pectate lyases, xyloglucanases (=xylases), pullulanases, and 3-glucanases.

In order to increase the bleaching effect, oxidoreductases such as oxidases, oxygenases, catalases, peroxidases such as halo-, chloro-, bromo-, lignin-, glucose-, or manganese peroxidases, dioxygenases or laccases (phenoloxidases, polyphenoloxidases) can be used if desired. Advantageously, organic, particularly preferably aromatic compounds that interact with the enzymes are additionally added in order to potentiate the activity of the relevant oxidoreductases (enhancers) or, in the event of greatly differing redox potentials, to ensure the flow of electrons between the oxidizing enzymes and the contaminants (mediators).

The enzymes can be used in any form established in the prior art. These include, for example, the solid preparations obtained by way of granulation, extrusion, or lyophilization or, particularly in the case of liquid or gel agents, solutions of the enzymes, advantageously maximally concentrated, low-moisture, and/or supplemented with stabilizers. Alternatively, the enzymes can also be encapsulated, for both the solid and the liquid administration form, for example by spray-drying or extrusion of the enzyme solution together with a preferably natural polymer or in the form of capsules, for example those in which the enzymes are enclosed in a set gel, or in those of the core-shell type, in which an enzyme-containing core is coated with a water-, air-, and/or chemical-impermeable protective layer. Other active ingredients such as stabilizers, emulsifiers, pigments, bleaching agents, or dyes can additionally be applied in overlaid layers. Such capsules are applied using inherently known methods, for example by shaking or roll granulation or in fluidized bed processes. Such granules are advantageously low in dust, for example due to the application of polymeric film-formers, and stable in storage due to the coating. Moreover, it is possible to formulate two or more enzymes together, such that a single granule exhibits a plurality of enzyme activities.

One or more enzymes and/or enzyme preparations, preferably protease preparations and/or amylase preparations, are preferably used in amounts of from 0.1 wt. % to 5 wt. %, preferably from 0.2 wt. % to 4.5 wt. %, and in particular from 0.4 wt. % to 4 wt. %.

Individual odorant compounds, such as synthetic products of the ester, ether, aldehyde, ketone, alcohol, and hydrocarbon types, can be used as perfume oils or fragrances. However, mixtures of different odorants are preferably used which together produce an appealing fragrance note. Perfume oils of this kind can also contain natural odorant mixtures, as are obtainable from plant sources, for example pine, citrus, jasmine, patchouli, rose or ylang-ylang oil. In order to be perceptible, an odorant must be volatile, wherein, in addition to the nature of the functional groups and the structure of the chemical compound, the molar mass also plays an important role. Therefore, most odorants have molar masses of up to approximately 200 g/mol, whereas molar masses of 300 g/mol and above represent something of an exception. Due to the differing volatility of odorants, the odor of a perfume or fragrance composed of multiple odorants varies over the course of vaporization, wherein the odor impressions are divided into "top note", "middle note or body" and "end note or dry out." Because the perception of an odor also depends to a large extent on the odor intensity, the top note of a perfume or fragrance does not only consist of highly volatile compounds, while the end note consists for the most part of less volatile, i.e. adherent, odorants. When composing perfumes, more volatile odorants can be bound, for example, to specific fixatives, thereby preventing them from evaporating too quickly. The subdivision below of odorants into "more volatile" and "adherent" odorants is therefore not a statement with regard to the odor impression, and, moreover, as to whether the corresponding odorant is perceived as a top or middle note. The fragrances can be processed directly, but it can also be advantageous to apply the fragrances to carriers which ensure long-lasting fragrance by slowly releasing the fragrance. Cyclodextrins have been found to be expedient as carrier materials of this kind, it also being possible to additionally coat the cyclodextrin perfume complexes with further auxiliaries.

When choosing the dye, it should be noted that the dye can have a high storage stability and sensitivity to light and not have an excessive affinity for textile surfaces and in this case in particular for synthetic fibers. It should also be noted that dyes can have different stabilities with respect to oxidation. Water-insoluble dyes are generally more stable against oxidation than water-soluble dyes. The concentration of the dye in the washing or cleaning agents varies depending on the solubility and therefore also on the sensitivity to oxidation. For highly water-soluble dyes, dye concentrations in the range of a few $10^{-2}$ wt. % to $10^{-3}$ wt. % are typically selected. However, for the pigment dyes that are preferred in particular due to their brightness, but are however less water-soluble, the suitable concentration of the dye in washing or cleaning agents is typically from a few $10^{-3}$ wt. % to $10^{-4}$ wt. %. Dyes which can be oxidatively destroyed in the washing process, and mixtures thereof with suitable blue dyes, which are referred to as blue toners, are preferred. It has been shown to be advantageous to use dyes which are soluble in water or in liquid organic substances at room temperature. For example, anionic dyes, for example anionic nitroso dyes, are suitable.

In addition to the previously mentioned components, the washing or cleaning agents can contain further ingredients which further improve the practical and/or aesthetic properties of these agents. Preferred agents contain one or more substances from the group of electrolytes, pH adjusting agents, fluorescing agents, hydrotropes, foam inhibitors, silicone oils, anti-redeposition agents, optical brighteners, graying inhibitors, anti-shrink agents, anti-crease agents, dye transfer inhibitors, antimicrobial active ingredients, germicides, fungicides, antioxidants, antistatic agents, ironing aids, repellents and impregnating agents, anti-swelling and anti-slip agents, and UV absorbers.

A large number of a wide range of salts can be used as electrolytes from the group of inorganic salts. Preferred cations are the alkali and alkaline-earth metals, preferred anions are the halides and sulfates. From a technical manufacturing point of view, the use of $NaCl$ or $MgCl_2$ in the washing or cleaning agents is preferred.

In order to bring the pH of washing or cleaning agents into the desired range, the use of pH adjusting agents can be advisable. In this case, all known acids or liquors can be used, provided the use thereof is not prohibited for practical or ecological reasons or for reasons of consumer protection. The amount of this adjuster does not usually exceed 1 wt. % of the total formulation.

Soaps, oils, fats, paraffins or silicone oils are possible foam inhibitors, which can optionally be applied to carrier materials. Suitable carrier materials include, for example, inorganic salts such as carbonates or sulfates, cellulose derivatives or silicates and mixtures of the aforementioned materials. Within the scope of the present invention, preferred agents contain paraffins, preferably unbranched paraffins (n-paraffins), and/or silicons, preferably linear-polymeric silicons, which are composed according to the formula $(R_2SiO)x$ and are also referred to as silicone oils. These silicone oils represent usually clear, colorless, neutral, odorless, hydrophobic liquids having a molecular weight between 1000 g/mol and 150,000 g/mol and viscosities between 10 mPa·s and 1,000,000 mPa·s.

Soil repellents include the polymers of phthalic acid and/or terephthalic acid known from the prior art and the derivatives thereof, in particular polymers from ethylene terephthalate and/or polyethylene glycol terephthalate or anionically and/or non-ionically modified derivatives thereof. Of these, the sulfonated derivatives of phthalic acid polymers and terephthalic acid polymers are particularly preferred.

Optical brighteners can in particular be added to the washing agents in order to eliminate graying and yellowing of the treated textiles. These substances absorb into the fibers and cause a lightening and pretend bleach effect, by converting invisible ultraviolet radiation into visible long-wave light, the ultraviolet light absorbed from the sunlight being emitted as light-blue fluorescence and, together with the yellow tone of the grayed or yellowed laundry, producing pure white. Suitable compounds originate for example from the substance classes of 4,4'-diamino-2,2'-stilbene disulfonic acids (flavonic acid), 4,4'-distyrylbiphenylene, methylumbelliferone, cumarines, dihydroquinolones, 1,3-diarylpyrazolines, naphthalic acid imides, benzoxazole systems, benzisoxazole systems, benzimidazole systems and pyrene derivatives substituted with heterocycles.

The function of graying inhibitors is to keep the dirt removed from the fibers suspended in the liquor and to therefore prevent the redeposition of the dirt. Water-soluble colloids, which are usually organic, are suitable for this purpose, for example the water-soluble salts of polymeric carboxylic acids, sizing material, gelatin, salts of ethersulfonic acids of starch or cellulose, or salts of acidic sulfuric acid esters of cellulose or starch. Water-soluble polyamides containing acid groups are also suitable for this purpose. Soluble starch preparations can also be used, for example degraded starch and aldehyde starches. Polyvinylpyrrolidone is also suitable. Cellulose ethers such as carboxymethyl cellulose (Na salt), methyl cellulose, hydroxyalkyl cellulose, and mixed ethers such as methylhydroxyethyl cellulose, methylhydroxypropyl cellulose, methylcarboxymethyl cellulose and mixtures thereof, can also be used as graying inhibitors. Non-ionic cellulose ethers such as methylcellulose and methylhydroxypropyl cellulose having a proportion of methoxy groups of from 15 to 30 wt. % and of hydroxypropyl groups of from 1 to 15 wt. %, in each case based on the non-ionic cellulose ether, are particularly suitable, for example.

Since textile fabrics, in particular those made of rayon, spun rayon, cotton and mixtures thereof, can tend to crease, because the individual fibers are sensitive to bending, kinking, pressing and crushing transversely to the fiber direction, synthetic anti-crease agents can be used. These include, for example, synthetic products based on fatty acids, fatty acid esters, fatty acid amides, fatty acid alkylol esters, fatty acid alkylolamides or fatty alcohols which are mostly reacted with ethylene oxide, or products based on lecithin or modified phosphoric acid ester.

Repellant and impregnating methods are used to finish the textiles with substances which prevent the deposition of dirt or make it easier to wash said dirt out. Preferred repellants and impregnating agents are perfluorated fatty acids, also in the form of the aluminum and zirconium salts thereof, organic silicates, silicons, polyacrylic acid esters having perfluorated alcohol components, or polymerizable compounds coupled to a perfluorated acyl or sulfonyl functional group. Antistatic agents can also be contained. The dirt-repellant finishing using repellants and impregnating agents is often classed as easy-care finishing. It is possible to facilitate the penetration of impregnating agents in the form of solutions or emulsions of the relevant active ingredients by adding wetting agents which reduce the surface tension. A further field of application of repellants and impregnating agents is the water-repellant finishing of textile goods, tents, tarpaulins, leather, etc., in which, in contrast to waterproofing, the fabric pores are not closed and the substance therefore remains breathable (hydrophobizing). The hydrophobizing agents used for hydrophobizing coat textiles, leather, paper, wood, etc. with a very thin layer of hydrophobic groups, such as longer alkyl chains or siloxane groups. Suitable hydrophobizing agents are, for example, paraffins, waxes, metal soaps etc. having additives of aluminum or zirconium salts, quaternary ammonium compounds having long-chain alkyl functional groups, urea derivatives, fatty acid-modified melamine resins, chromium complex salts, silicons, organotin compounds and glutardialdehyde and perfluorinated compounds. The hydrophobized materials do not feel oily; instead, similar to oiled substances, water droplets drip off said materials without wetting them. Silicon-impregnated textiles, for example, therefore have a soft feel and are water and dirt repellent; marks from ink, wine, fruit juices and the like are easier to remove.

Antimicrobial active ingredients can be used to combat microorganisms. Here a distinction is made, depending on the antimicrobial spectrum and mechanism of action, between bacteriostatic agents and bactericides, fungistatic agents and fungicides, and so forth. Substances from these groups are, for example, benzalkonium chlorides, alkylarlyl sulfonates, halophenols and phenylmercury acetate, it also being possible to omit these compounds entirely.

In order to prevent undesired changes to the washing agents and/or to the treated textiles that are caused by the effect of atmospheric oxygen and other oxidative processes, the agents can contain antioxidants. This compound class includes, for example, substituted phenols, hydroquinones, pyrocatechols and aromatic amines, and organic sulfides, polysulfides, dithiocarbamates, phosphites and phosphonates.

Increased wearing comfort can result from the additional use of antistatic agents. Antistatic agents increase the surface conductivity and therefore facilitate improved discharge of charges formed. External antistatic agents are generally substances that have at least one hydrophilic molecule ligand and produce a more or less hygroscopic film on the surface. These predominantly surface-active antistatic agents can be divided into nitrogen-containing antistatic agents (amines, amides, quaternary ammonium compounds), phosphorous-containing antistatic agents (phosphoric acid esters) and sulfur-containing antistatic agents (alkyl sulfonates, alkyl sulfates). Lauryl (or stearyl) dimethyl benzyl ammonium chlorides are also suitable as antistatic agents for textiles or as an additive in washing agents, a softening effect additionally being achieved.

Silicone derivatives can be used in textile detergents in order to improve the water-absorption capability and the re-wettability of the treated textiles and in order to facilitate ironing of the treated textiles. These also improve the rinsing behavior of washing or cleaning agents as a result of the foam-inhibiting properties thereof. Preferred silicone derivatives are, for example, polydialkyl siloxanes or alkylaryl siloxanes, in which the alkyl groups have 1 to 5 C atoms and are completely or partially fluorinated. Preferred silicones are polydimethylsiloxanes, which can optionally be derivatized and are then aminofunctional or quaternized, or have Si—OH—, Si—H— and/or Si—Cl— bonds. Further preferred silicons are polyalkylene oxide-modified polysiloxanes, i.e. polysiloxanes which comprise, for example, polyethylene glycol, and polyalkylene oxide-modified dimethylpolysiloxanes.

Lastly, UV absorbers can also be used which absorb into the treated textiles and improve the light resistance of the fibers. Compounds which have these desired properties are, for example, the active compounds from non-radiative deactivation and derivatives of benzophenone having substituents in the 2 and/or 4 position. Substituted benzotriazoles, acrylates that are phenyl-substituted in the 3 position (cinnamic acid derivatives), optionally having cyano groups in the 2 position, salicylates, organic Ni complexes and natural substances such as umbelliferone and the endogenous urocanic acid are also suitable.

Protein hydrolyzates are further suitable active substances due to the fiber-caring effect thereof. Protein hydrolyzates are product mixtures that are obtained by acid-, base-, or enzyme-catalyzed degradation of proteins. Protein hydrolyzates of both plant and animal origin can be used. Animal protein hydrolyzates are, for example, elastin, collagen, keratin, silk, and milk protein hydrolyzates, which can also be present in the form of salts. It is preferable to use protein hydrolyzates of plant origin, for example soybean, almond, rice, pea, potato and wheat protein hydrolyzates. Although the use of protein hydrolyzates is preferred as such, amino acid mixtures otherwise obtained or individual amino acids such as arginine, lysine, histidine or pyroglutamic acid can optionally also be used in their place. The use of derivatives of protein hydrolyzates, for example in the form of the fatty acid condensation products thereof, is also possible.

EXAMPLES

Example 1: Synthesis of Compounds According to the Invention

1. Synthesis and Analysis of 3-(($^{tert}$butyldiphenylsilyl)oxy)-2-methyl-4H-pyran-4-one (3c)

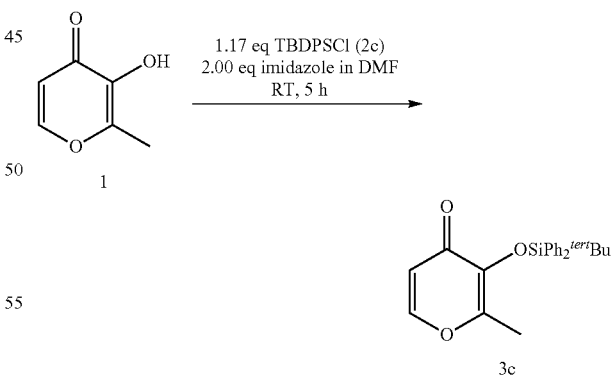

2.52 g (20.0 mmol) of maltol (1) and 6.42 g (23.4 mmol) of tert-butyldiphenylsilyl chloride TBDPSCl (2c) were provided in a purged Schlenk flask and dissolved in 50 ml of dry N,N-dimethylformamide. It was stirred for 10 min at room temperature (20° C.) until completely dissolved. After this time, 2.73 g (40.0 mmol) of imidazole was added in one portion and then stirred for 5 h at 20° C. After the elapsed reaction time, saturated sodium bicarbonate solution was added to the reaction mixture until no generation of gas could be observed. The resulting solid was dissolved by adding deionized water and the aqueous phase was subsequently extracted four times with 250 ml of an n-hexane-ethyl acetate mixture (1:1, v/v) in each case. The organic phases were combined and dried using anhydrous sodium sulfate. Finally, the crude product obtained was purified by column chromatography on silica gel using a solvent mixture consisting of n-hexane and ethyl acetate (3:1, v/v). 7.03 g (19.3 mmol, 96%) of product 3c was obtained in the form of a colorless solid.

Melting point: 127° C.
Rf value (n-hexane: EtOAc, 5:1): 0.22
$^1$H-NMR (300 MHz, chloroform-d): δ=1.08 (s, 9H), 2.37 (s, 3H), 6.09 (d, J=5.6 Hz, 1H), 7.30-7.42 (m, 6H), 7.48 (d, J=5.6 Hz, 1H), 7.69-7.73 (m, 4H).

2.a) General Procedure for the Amination of the Protected Maltol Precursor 3c

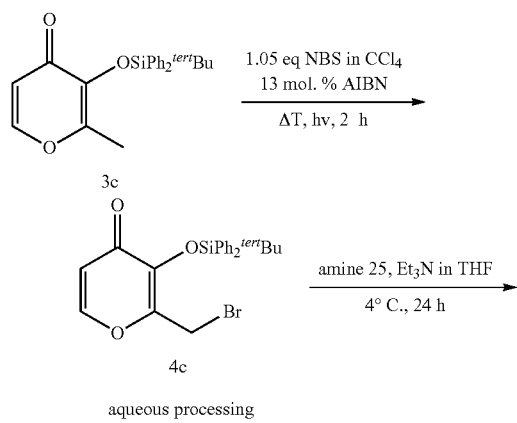

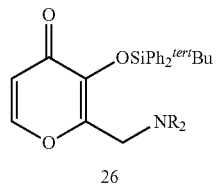

26

The pyrone 3c was provided in a purged Schlenk tube and dissolved in 5 ml of tetrachloromethane. 187 mg (1.05 mmol) of N-bromosuccinimide was subsequently added and the reaction mixture was heated to 96° C. After 15 min, 21.9 mg (13 mol. %) of azobis(isobutyronitrile) was added in nitrogen countercurrent and the reaction mixture was heated in an oil bath for 2 h by means of irradiation using a UV lamp. The reaction mixture was subsequently cooled and received in dichloromethane. The solution was washed twice using saturated aqueous sodium hydrogen carbonate solution. The combined aqueous phases were extracted three times with 10 ml of dichloromethane in each case. The combined organic phases were washed using saturated aqueous sodium chloride solution and the aqueous phase was extracted twice with 10 ml of dichloromethane in each case. The combined organic phases were dried using anhydrous Na$_2$SO$_4$ and the solvent was completely distilled off. The crude product obtained was dissolved in 4 ml of tetrahydrofuran. 5 ml of tetrahydrofuran was provided in a purged 50 ml two-necked flask and the amine 25 was added. The flask was cooled to 4° C. in the refrigerator, then triethylamine was added, swirled and cooled again in the refrigerator for at least 30 min. After this time, the crude product dissolved in tetrahydrofuran was added rapidly in three portions and the reaction mixture was stored in the refrigerator for 24 h. It was then warmed to room temperature and processed as described above. The obtained crude product was adsorbed onto Celite® and purified by column chromatography on silica gel.

| Pyrone 3c mg (mmol) | Amine 25 mg (mmol) | Triethylamine mg (mmol) | Product 26 Yield in mg (%) |
|---|---|---|---|
| 365 (1) | HN⌒NH  25b  41.2 (0.47) | 134 (1.32) | 26c  237 (62)  R = –SiPh$_2$$^{tert}$Bu |
| 365 (1) | MeHN(CH$_2$)$_3$NHMe  25c  48.4 (0.46) | 135 (1.33) | 26d  204 (54)  R = –SiPh$_2$$^{tert}$Bu |

| Pyrone 3c mg (mmol) | Amine 25 mg (mmol) | Triethylamine mg (mmol) | Product 26 Yield in mg (%) |
|---|---|---|---|
| 365 (1) | 25d 39.7 (0.46) | 135 (1.33) | 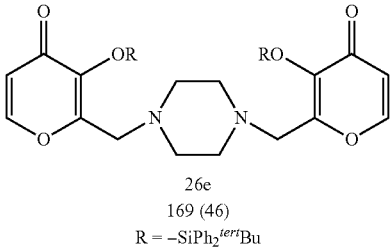 26e 169 (46) R = –SiPh$_2$$^{tert}$Bu |

2.b) Preparation of 2,2'-((ethane-1,2-diyl-bis(methylazandiyl))bis(methylene))bis(3-((tert-butyldiphenylsilyl)oxy)-4H-pyran-4-one) (26c)

Similarly to the general procedure (2.a), after column chromatographic purification on silica gel using a mixture consisting of n-hexane and ethyl acetate (1:1, v/v) and a methanol gradient (0% after 10% v/v) as eluents, 237 mg (0.29 mmol, 62%) of product 26c was obtained as a slightly orange, analytically pure solid.

Melting point: 194° C.

Rf value (CH$_2$Cl$_2$:MeOH, 10:1): 0.47

$^1$H-NMR (300 MHz, chloroform-d): δ=1.05 (s, 18H), 2.40 (s, 6H), 2.73 (s (wide), 4H), 3.80 (s (wide), 4H), 6.09 (d, J=5.6 Hz, 2H), 7.27-7.41 (m, 12H), 7.55 (d, J=5.6 Hz, 2H), 7.61-7.75 (m, 8H).

2.c) Preparation of 2,2'-((propane-1,3-diylbis(methylazandiyl))bis(methylene))bis(3-((tert-butyldiphenylsilyl)oxy)-4H-pyran-4-one) (26d)

Similarly to the general procedure (2.a), after column chromatographic purification on silica gel using a mixture consisting of n-hexane and ethyl acetate (1:1, v/v) and a methanol gradient (0% after 10% v/v) as eluents, 204 mg (0.25 mmol, 54%) of product 26d was obtained as a slightly orange, analytically pure solid.

Melting point: 145° C.

Rf value (CH$_2$Cl$_2$:MeOH, 10:1): 0.36

$^1$H-NMR (300 MHz, chloroform-d): δ=1.05 (s, 18H), 1.71-1.86 (m, 2H), 2.37 (s, 6H), 2.55 (t, J=7.2 Hz, 4H), 3.72 (s, 4H), 6.07 (d, J=5.6 Hz, 2H), 7.28-7.41 (m, 12H), 7.53 (d, J=5.6 Hz, 2H), 7.67-7.70 (m, 8H).

2.d) Preparation of 2,2'-(piperazine-1,4-diylbis(methylene))bis(3-((tert-butyldiphenylsilyl)oxy)-4H-pyran-4-one) (26e)

Similarly to the general procedure (2.a), after column chromatographic purification on silica gel using a mixture consisting of n-hexane and ethyl acetate (1:1, v/v) and a methanol gradient (0% after 10% v/v) as eluents, 169 mg (0.21 mmol, 46%) of the product 26e was obtained as a slightly beige, analytically pure solid.

Melting point: 240° C.

$^1$H-NMR (300 MHz, chloroform-d): δ=1.05 (s, 18H), 2.69 (s (wide), 8H), 3.76 (s, 4H), 6.10 (d, J=5.6 Hz, 2H), 7.27-7.42 (m, 12H), 7.60 (d, J=5.6 Hz, 2H), 7.64-7.73 (m, 8H).

3. Preparation of 2,2'-((ethane-1,2-diylbis(methylazanediyl))bis(methylene))bis(3-hydroxy-4H-pyran-4-one) hydrochloride (28b)

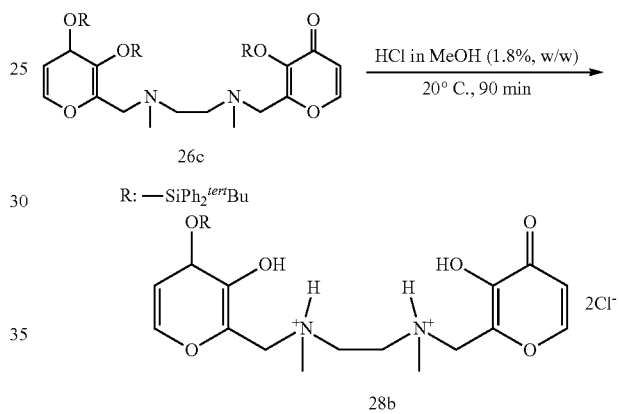

5 g of concentrated hydrochloric acid was added slowly into 95 g of methanol. 407 mg (0.50 mmol) of the malto derivate 26c was provided in a purged Schlenk tube, and the vessel was evacuated again and aerated with nitrogen. Subsequently, 2.5 ml of the HCl solution was added in nitrogen countercurrent while stirring. After 15 min, the yellow clear reaction solution became cloudy and a colorless solid was precipitated. After 90 minutes the reaction mixture was processed. The resulting solid was washed three times using methanol. After drying in a high vacuum, 152 mg (0.37 mmol, 74%) of 28b was obtained in the form of a colorless solid. Moreover, an additional 42 mg (0.10 mmol, 20%) of product 28b could be obtained from the mother liquor after distilling off the solvent and resuspending three times in dichloromethane. This corresponds to a total yield of 194 mg (0.47 mmol, 94%).

$^1$H-NMR (300 MHz, deuterium oxide-d2): δ=3.03 (s, 6H), 3.79 (s(wide), 4H), 4.59 (s (wide), 4H), 6.62 (d, J=5.6 Hz, 2H), 8.13 (d, J=5.6 Hz, 2H).

$^{13}$C-NMR (75 MHz, D20): δ=41.7 (2 CH$_3$), 50.1 (2 CH$_2$), 52.9 (2 CH$_2$), 114.8 (2 CH), 141.3 (2 C$_{quart}$), 147.6 (2 C$_{quart}$), 157.9 (2 CH), 176.1 (2 C$_{quart}$).

Similarly, 26d and 26e were deprotected to form the compounds 28c and 28d.

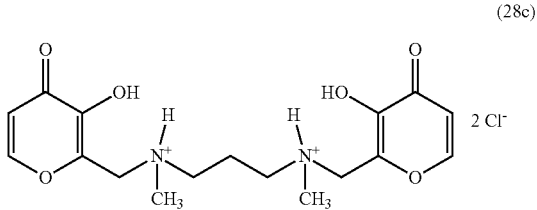

(28c)

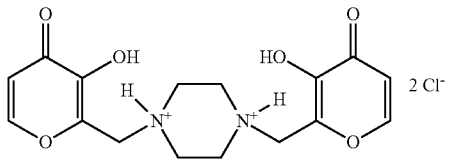

(28d)

Example 2: Cleaning Performance

Washing tests were carried out at 40° C. on various stains specified in Table 1 below, which stains are based on polyphenolic natural dyes (flavonoids). The test stains were prepared manually by dosing a constant amount of a dilute aqueous solution of the specified extracts onto cotton fabric and then drying. For the washing tests, a bleaching agent-free liquid detergent (FWM) was used and washing liquors having pH 8.5 were prepared therewith, the liquors consisting of 69 g FWM and optionally 1.4 g of one of the active ingredients also specified in Table 1 to 171 of water of 16° dH. The evaluation was completed by measuring the color distance according to the L*a*b* vales and the Y values calculated therefrom as a measure for brightness. The following table shows the improvement in stain removal as the difference (difference Y (after washing)-Y (before washing)) between the FWM formulation with added active ingredient and the FWM without added active ingredient as mean values of triple determination.

TABLE 1

| Differences in brightness difference | | | |
|---|---|---|---|
| Stain comprising extract from | FWM + 28b | FWM + 28c | FWM + 28d |
| Blueberry | 6.3 | 4.7 | 5.5 |
| Bilberry | 5.4 | 3.7 | 3.7 |

The dY values with the addition of an active ingredient used according to the invention were always greater than the values obtained using the FWM without the addition, and this corresponds to a higher degree of whiteness and thus improved stain removal.

What is claimed is:

1. A method for washing or cleaning stains comprising a step of contacting a fabric comprising stains with washing or cleaning agents having a compound of general formula (I),

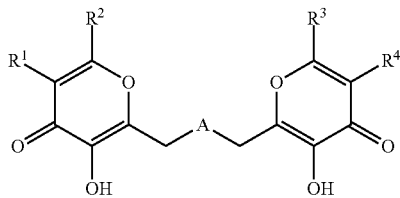

(I)

in which A represents —Q—(CH$_2$)$_n$—Q, —(CH$_2$)$_m$—Q—(CH$_2$)$_p$— or

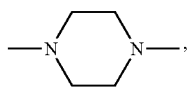

Q represents O, N(R$^5$) or N$^+$H(R$^5$) X$^-$, R$^1$, R$^2$, R$^3$, R$^4$ and R$^5$ represent, independently of one another, hydrogen or a straight-chain or branched unsubstituted alkyl group having 1 to 4 C atoms, X$^-$ represents a charge-balancing anion, and n represents a number from 1 to 10, and m and p represent, independently of one another, numbers from 0 to 7.

2. The method according to claim 1, wherein the stains comprise polymerizable substances selected from polyphenolic dyes.

3. The method according to claim 1 wherein the washing or cleaning comprises improved removal of green, yellow, red, blue, violet, lilac, brown, purple or pink colored stains.

4. The method according to claim 1, wherein the stains are selected from stains caused by cherries, morellos, grapes, apples, pomegranates, chokeberries, plums, sea buckthorns, acai berries, kiwis, mangoes, grass or berries.

5. A washing or cleaning agent comprising a compound of the general formula (I),

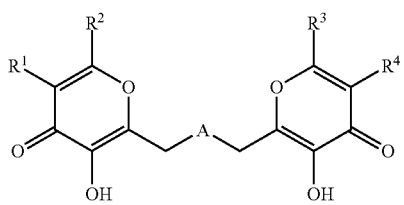

(I)

in which A represents —Q—(CH$_2$)$_n$—Q, —(CH$_2$)$_m$—Q—(CH$_2$)$_p$— or

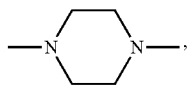

Q represents O, N(R$^5$) or N$^+$H(R$^5$)X$^-$, R$^1$, R$^2$, R$^3$, R$^4$ and R$^5$ represent, independently of one another, hydrogen or a straight-chain or branched unsubstituted alkyl group having 1 to 4 C atoms, X$^-$ represents a charge-balancing anion, and n represents a number from 1 to 10, and m and p represent, independently of one another, numbers from 0 to 7.

6. The agent according to claim 5, wherein the agent contains 0.001 wt. % to 20 wt. % of a compound of general formula (I).

7. The agent according to claim 5, wherein it does not contain hypochlorites, hydrogen peroxide or substances that yield hydrogen peroxide, and peroxoacids.

8. The agent according to claim 5, wherein the agent further comprises a component selected from the group consisting of builders, surfactants, and mixtures thereof.

9. The agent according to claim 5, wherein in the compounds of the general formula (I), $R^1$ and $R^3$ and/or $R^2$ and $R^4$ are the same.

10. The agent according to claim 5, wherein in the compounds of the general formula (I), $R^1$, $R^2$, $R^3$ and $R^4$ are hydrogen, and/or $R^5$ is a methyl group, and/or n is a number from 1 to 6.

11. The method according to claim 2, wherein the stains comprise polymerizable substances selected from flavonoids.

12. The method according to claim 2, wherein the stains comprise polymerizable substances selected from dyes from the class of anthocyanidins.

13. The method according to claim 1, wherein the stains comprise polymerizable substances selected from dyes from the class of anthocyanins.

14. The method according to claim 1, wherein the washing or cleaning comprises improved removal of marks from grass, fruit or vegetables, which contain the corresponding green, yellow, red, violet, lilac, brown, purple, pink and/or blue dyes.

15. The method according to claim 1, wherein the washing or cleaning comprises improved removal of stains caused by food products or drinks, which contain the corresponding green, yellow, red, violet, lilac, brown, purple, pink and/or blue dyes.

16. The method according to claim 1, wherein the washing or cleaning comprises improved removal of stains caused by spices, sauces, chutneys, curries, purees, jams, coffee, tea, wine and juices, which contain the corresponding green, yellow, red, violet, lilac, brown, purple, pink and/or blue dyes.

17. The method according to claim 1, wherein the stains are selected from stains caused by redcurrants, blackcurrants, elderberries, blackberries, raspberries, blueberries, lingonberries, cranberries, strawberries or bilberries, or by coffee, tea, red cabbage, blood orange, eggplant, tomato, carrot, beetroot, spinach, bell pepper, red or blue potato or red onion.

18. The agent according to claim 6, wherein the agent contains 0.01 wt. % to 10 wt. % of the compound of general formula (I).

19. The agent according to claim 10, wherein, in the compounds of the general formula (I), n is a number from 1 to 3.

* * * * *